(12) United States Patent
Stoklund et al.

(10) Patent No.: US 8,043,378 B2
(45) Date of Patent: Oct. 25, 2011

(54) INTERCOSTAL SPACER DEVICE AND METHOD FOR USE IN CORRECTING A SPINAL DEFORMITY

(75) Inventors: Ole Stoklund, Germantown, TN (US); Kent M. Anderson, Sunnyvale, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 29 days.

(21) Appl. No.: 12/471,990

(22) Filed: May 26, 2009

(65) Prior Publication Data

US 2009/0227990 A1 Sep. 10, 2009

Related U.S. Application Data

(63) Continuation-in-part of application No. 11/470,810, filed on Sep. 7, 2006, now abandoned.

(51) Int. Cl.
*A61F 2/44* (2006.01)

(52) U.S. Cl. ............... 623/17.11; 606/248; 606/249

(58) Field of Classification Search .......... 606/248–249; 623/17.11–17.16
See application file for complete search history.

(56) References Cited

U.S. PATENT DOCUMENTS

| | | |
|---|---|---|
| 624,969 A | 5/1899 | Peterson |
| 1,153,797 A | 9/1915 | Kegreisz |
| 1,516,347 A | 11/1924 | Pataky |
| 1,870,942 A | 8/1932 | Beatty |
| 2,077,804 A | 4/1937 | Morrison |
| 2,299,308 A | 10/1942 | Creighton |
| 2,485,531 A | 10/1949 | Dzus et al. |
| 2,607,370 A | 8/1952 | Anderson |
| 2,677,369 A | 5/1954 | Knowles |
| 2,685,877 A | 8/1954 | Dobelle |
| 3,065,659 A | 11/1962 | Eriksson et al. |
| 3,108,595 A | 10/1963 | Overment |
| 3,426,364 A | 2/1969 | Lumb |
| 3,648,691 A | 3/1972 | Lumb et al. |
| 3,779,239 A | 12/1973 | Fischer et al. |
| 3,867,728 A | 2/1975 | Stubstad et al. |
| 4,011,602 A | 3/1977 | Rybicki et al. |
| 4,237,875 A | 12/1980 | Termanini |
| 4,257,409 A | 3/1981 | Bacal et al. |
| 4,274,324 A | 6/1981 | Giannuzzi |
| 4,289,123 A | 9/1981 | Dunn |
| 4,401,112 A | 8/1983 | Rezaian |
| 4,499,636 A | 2/1985 | Tanaka |
| 4,519,100 A | 5/1985 | Wills et al. |

(Continued)

FOREIGN PATENT DOCUMENTS

DE 2821678 A1 11/1979

(Continued)

OTHER PUBLICATIONS

"Dispositivo Intervertebrale Ammortizzante DIAM," date unknown, p. 1.

(Continued)

*Primary Examiner* — Eduardo C Robert
*Assistant Examiner* — Julianna N Harvey

(57) ABSTRACT

An intercostal spacer device for placement between two adjacent ribs, includes a spacer member and at least two pair of arms that extend from a first end of the spacer member and at least one pair of arms that extend from a second end of the spacer member. The intercostal spacer device is sized and configured to allow for placement into the intercostal space to produce a force for correcting a spinal deformity.

19 Claims, 7 Drawing Sheets

U.S. PATENT DOCUMENTS

| | | |
|---|---|---|
| 4,553,273 A | 11/1985 | Wu |
| 4,554,914 A | 11/1985 | Kapp et al. |
| 4,573,454 A | 3/1986 | Hoffman |
| 4,592,341 A | 6/1986 | Omagari et al. |
| 4,599,086 A | 7/1986 | Doty |
| 4,604,995 A | 8/1986 | Stephens et al. |
| 4,611,582 A | 9/1986 | Duff |
| 4,632,101 A | 12/1986 | Freedland |
| 4,636,217 A | 1/1987 | Ogilvie et al. |
| 4,646,998 A | 3/1987 | Pate |
| 4,657,550 A | 4/1987 | Daher |
| 4,662,808 A | 5/1987 | Camilleri |
| 4,686,970 A | 8/1987 | Dove et al. |
| 4,704,057 A | 11/1987 | McSherry |
| 4,759,769 A | 7/1988 | Hedman et al. |
| 4,787,378 A | 11/1988 | Sodhi |
| 4,822,226 A | 4/1989 | Kennedy |
| 4,827,918 A | 5/1989 | Olerud |
| 4,834,600 A | 5/1989 | Lemke |
| 4,863,476 A | 9/1989 | Shepperd |
| 4,886,405 A | 12/1989 | Blomberg |
| 4,892,545 A | 1/1990 | Day et al. |
| 4,913,144 A | 4/1990 | Del Medico |
| 4,931,055 A | 6/1990 | Bumpus et al. |
| 4,932,975 A | 6/1990 | Main et al. |
| 4,969,887 A | 11/1990 | Sodhi |
| 4,969,888 A | 11/1990 | Scholten et al. |
| 5,000,166 A | 3/1991 | Karpf |
| 5,011,484 A | 4/1991 | Breard |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,171,278 A | 12/1992 | Pisharodi |
| 5,171,280 A | 12/1992 | Baumgartner |
| 5,201,734 A | 4/1993 | Cozad et al. |
| 5,267,999 A | 12/1993 | Olerud |
| 5,290,312 A | 3/1994 | Kojimoto et al. |
| 5,306,275 A | 4/1994 | Bryan |
| 5,306,310 A | 4/1994 | Siebels |
| 5,312,405 A | 5/1994 | Korotko et al. |
| 5,360,430 A | 11/1994 | Lin |
| 5,366,455 A | 11/1994 | Dove |
| 5,370,697 A | 12/1994 | Baumgartner |
| 5,390,683 A | 2/1995 | Pisharodi |
| 5,395,370 A | 3/1995 | Muller et al. |
| 5,401,269 A | 3/1995 | Buttner-Janz et al. |
| 5,403,316 A | 4/1995 | Ashman |
| 5,415,661 A | 5/1995 | Holmes |
| 5,437,672 A | 8/1995 | Alleyne |
| 5,437,674 A | 8/1995 | Worcel et al. |
| 5,439,463 A | 8/1995 | Lin |
| 5,454,812 A | 10/1995 | Lin |
| 5,458,641 A | 10/1995 | Ramirez Jimenez |
| 5,480,442 A | 1/1996 | Bertagnoli |
| 5,496,318 A | 3/1996 | Howland et al. |
| 5,518,498 A | 5/1996 | Lindenberg et al. |
| 5,549,679 A | 8/1996 | Kuslich |
| 5,554,191 A | 9/1996 | Lahille et al. |
| 5,562,662 A | 10/1996 | Brumfield et al. |
| 5,562,735 A | 10/1996 | Margulies |
| 5,562,736 A | 10/1996 | Ray et al. |
| 5,571,192 A | 11/1996 | Schonhoffer |
| 5,609,634 A | 3/1997 | Voydeville |
| 5,609,635 A | 3/1997 | Michelson |
| 5,628,756 A | 5/1997 | Barker, Jr. et al. |
| 5,630,816 A | 5/1997 | Kambin |
| 5,645,597 A | 7/1997 | Krapiva |
| 5,645,599 A * | 7/1997 | Samani ............... 623/17.16 |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,674,295 A | 10/1997 | Ray et al. |
| 5,676,702 A | 10/1997 | Ratron |
| 5,685,826 A | 11/1997 | Bonutti |
| 5,690,649 A | 11/1997 | Li |
| 5,693,100 A | 12/1997 | Pisharodi |
| 5,702,395 A | 12/1997 | Hopf |
| 5,702,452 A | 12/1997 | Argenson et al. |
| 5,702,454 A | 12/1997 | Baumgartner |
| 5,702,455 A | 12/1997 | Saggar |
| 5,707,390 A | 1/1998 | Bonutti |
| 5,716,416 A | 2/1998 | Lin |
| 5,723,013 A | 3/1998 | Jeanson et al. |
| 5,725,341 A | 3/1998 | Hofmeister |
| 5,746,762 A | 5/1998 | Bass |
| 5,755,797 A | 5/1998 | Baumgartner |
| 5,800,547 A | 9/1998 | Schafer et al. |
| 5,800,549 A | 9/1998 | Bao et al. |
| 5,810,815 A | 9/1998 | Morales |
| 5,836,948 A | 11/1998 | Zucherman et al. |
| 5,849,004 A | 12/1998 | Bramlet |
| 5,860,977 A | 1/1999 | Zucherman et al. |
| 5,888,196 A | 3/1999 | Bonutti |
| 5,941,881 A | 8/1999 | Barnes |
| 5,964,730 A | 10/1999 | Williams et al. |
| 5,976,186 A | 11/1999 | Bao et al. |
| 5,980,523 A | 11/1999 | Jackson |
| 6,022,376 A | 2/2000 | Assell et al. |
| 6,048,342 A | 4/2000 | Zucherman et al. |
| 6,066,154 A | 5/2000 | Reiley et al. |
| 6,068,630 A | 5/2000 | Zucherman et al. |
| 6,126,689 A | 10/2000 | Brett |
| 6,126,691 A | 10/2000 | Kasra et al. |
| 6,127,597 A | 10/2000 | Beyar et al. |
| 6,132,464 A | 10/2000 | Martin |
| 6,190,413 B1 | 2/2001 | Sutcliffe |
| 6,190,414 B1 | 2/2001 | Young |
| 6,214,050 B1 | 4/2001 | Huene |
| 6,293,949 B1 | 9/2001 | Justis et al. |
| 6,336,930 B1 | 1/2002 | Stalcup et al. |
| 6,348,053 B1 | 2/2002 | Cachia |
| 6,352,537 B1 | 3/2002 | Strnad |
| 6,364,883 B1 | 4/2002 | Santilli |
| 6,371,987 B1 | 4/2002 | Weiland et al. |
| 6,375,682 B1 | 4/2002 | Fleischmann et al. |
| 6,402,750 B1 | 6/2002 | Atkinson et al. |
| 6,402,751 B1 | 6/2002 | Hoeck et al. |
| 6,419,704 B1 | 7/2002 | Ferree |
| 6,432,130 B1 | 8/2002 | Hanson |
| 6,440,169 B1 | 8/2002 | Elberg et al. |
| 6,447,513 B1 | 9/2002 | Griggs |
| 6,451,019 B1 | 9/2002 | Zucherman et al. |
| 6,500,178 B2 | 12/2002 | Zucherman et al. |
| 6,511,508 B1 | 1/2003 | Shahinpoor et al. |
| 6,514,256 B2 | 2/2003 | Zucherman et al. |
| 6,520,991 B2 | 2/2003 | Huene |
| 6,554,833 B2 | 4/2003 | Levy |
| 6,582,433 B2 | 6/2003 | Yun |
| 6,582,467 B1 | 6/2003 | Teitelbaum et al. |
| 6,592,585 B2 | 7/2003 | Lee et al. |
| 6,626,944 B1 | 9/2003 | Taylor |
| 6,645,207 B2 | 11/2003 | Dixon et al. |
| 6,685,742 B2 | 2/2004 | Jackson |
| 6,695,842 B2 | 2/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,533 B1 | 5/2004 | Lozier |
| 6,733,534 B2 | 5/2004 | Sherman |
| 6,736,818 B2 | 5/2004 | Perren et al. |
| 6,743,257 B2 | 6/2004 | Castro |
| 6,758,863 B2 | 7/2004 | Estes et al. |
| 6,761,720 B1 | 7/2004 | Senegas |
| 6,770,096 B2 | 8/2004 | Bolger et al. |
| 6,783,530 B1 | 8/2004 | Levy |
| 6,835,205 B2 | 12/2004 | Atkinson et al. |
| 6,905,512 B2 | 6/2005 | Paes et al. |
| 6,946,000 B2 | 9/2005 | Senegas et al. |
| 6,958,077 B2 | 10/2005 | Suddaby |
| 6,969,404 B2 | 11/2005 | Ferree |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,081,120 B2 | 7/2006 | Li et al. |

| Patent/Pub No. | Date | Name |
|---|---|---|
| 7,087,083 B2 | 8/2006 | Pasquet et al. |
| 7,097,648 B1 | 8/2006 | Globerman et al. |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,431,735 B2 | 10/2008 | Liu et al. |
| 7,442,208 B2 | 10/2008 | Mathieu et al. |
| 7,445,637 B2 | 11/2008 | Taylor |
| 7,458,981 B2 | 12/2008 | Fielding et al. |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 7,621,950 B1 | 11/2009 | Globerman et al. |
| 2001/0016743 A1 | 8/2001 | Zucherman et al. |
| 2002/0082600 A1 | 6/2002 | Shaolian et al. |
| 2002/0143331 A1 | 10/2002 | Zucherman et al. |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2004/0010312 A1 | 1/2004 | Enayati |
| 2004/0010316 A1 | 1/2004 | William et al. |
| 2004/0083002 A1 | 4/2004 | Belef et al. |
| 2004/0087947 A1 | 5/2004 | Lim et al. |
| 2004/0097931 A1 | 5/2004 | Mitchell |
| 2004/0133204 A1 | 7/2004 | Davies |
| 2004/0133280 A1 | 7/2004 | Trieu |
| 2004/0167625 A1 | 8/2004 | Beyar et al. |
| 2004/0199255 A1 | 10/2004 | Mathieu et al. |
| 2004/0260397 A1 | 12/2004 | Lambrecht et al. |
| 2005/0010293 A1 | 1/2005 | Zucherman et al. |
| 2005/0015140 A1 | 1/2005 | deBeer |
| 2005/0049708 A1 | 3/2005 | Atkinson et al. |
| 2005/0085814 A1 | 4/2005 | Sherman et al. |
| 2005/0102028 A1* | 5/2005 | Arnin et al. ............... 623/17.13 |
| 2005/0143827 A1 | 6/2005 | Globerman et al. |
| 2005/0165398 A1 | 7/2005 | Reiley |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0228391 A1 | 10/2005 | Levy et al. |
| 2005/0245937 A1 | 11/2005 | Winslow |
| 2005/0261768 A1 | 11/2005 | Trieu |
| 2005/0273166 A1 | 12/2005 | Sweeney |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 | 6/2006 | Taylor |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1* | 10/2006 | Anderson ............... 606/61 |
| 2006/0224241 A1 | 10/2006 | Butler et al. |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0271061 A1 | 11/2006 | Beyar et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0032790 A1 | 2/2007 | Aschmann et al. |
| 2007/0043362 A1 | 2/2007 | Malandain et al. |
| 2007/0073289 A1 | 3/2007 | Kwak et al. |
| 2007/0100340 A1 | 5/2007 | Lange et al. |
| 2007/0123861 A1 | 5/2007 | Dewey et al. |
| 2007/0142915 A1 | 6/2007 | Altarac et al. |
| 2007/0151116 A1 | 7/2007 | Malandain |
| 2007/0162000 A1 | 7/2007 | Perkins |
| 2007/0162136 A1 | 7/2007 | O'Neil et al. |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0198091 A1 | 8/2007 | Boyer et al. |
| 2007/0225807 A1 | 9/2007 | Phan et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0282443 A1 | 12/2007 | Globerman et al. |
| 2008/0021457 A1 | 1/2008 | Anderson et al. |
| 2008/0021460 A1 | 1/2008 | Bruneau et al. |
| 2008/0058934 A1 | 3/2008 | Malandain et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0183209 A1 | 7/2008 | Robinson et al. |
| 2008/0183211 A1 | 7/2008 | Lamborne et al. |
| 2008/0183218 A1 | 7/2008 | Mueller et al. |
| 2008/0215094 A1 | 9/2008 | Taylor |
| 2008/0221685 A9 | 9/2008 | Altarac et al. |
| 2008/0234824 A1 | 9/2008 | Youssef et al. |
| 2008/0262617 A1 | 10/2008 | Froehlich et al. |
| 2008/0281360 A1 | 11/2008 | Vittur et al. |
| 2008/0281361 A1 | 11/2008 | Vittur et al. |
| 2009/0062915 A1 | 3/2009 | Kohm et al. |
| 2009/0105766 A1 | 4/2009 | Thompson et al. |
| 2009/0105773 A1 | 4/2009 | Lange et al. |
| 2009/0234389 A1 | 9/2009 | Chuang et al. |
| 2009/0270918 A1 | 10/2009 | Attia et al. |
| 2010/0121379 A1 | 5/2010 | Edmond |

FOREIGN PATENT DOCUMENTS

| | | |
|---|---|---|
| DE | 3922044 A1 | 2/1991 |
| DE | 4012622 C1 | 7/1991 |
| EP | 0322334 B1 | 2/1992 |
| EP | 0767636 B1 | 1/1999 |
| EP | 1004276 A1 | 5/2000 |
| EP | 1011464 B1 | 6/2000 |
| EP | 1138268 A1 | 10/2001 |
| EP | 1148850 B1 | 10/2001 |
| EP | 1148851 B1 | 10/2001 |
| EP | 1302169 A1 | 4/2003 |
| EP | 1330987 A1 | 7/2003 |
| EP | 1552797 A2 | 7/2005 |
| EP | 1854433 A1 | 11/2007 |
| EP | 1905392 A1 | 4/2008 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| SU | WO 988281 | 1/1983 |
| SU | 1484348 A1 | 6/1989 |
| WO | WO 94/26192 | 11/1994 |
| WO | WO 94/26195 | 11/1994 |
| WO | WO 97/18769 | 5/1997 |
| WO | WO 98/20939 | 5/1998 |
| WO | WO 99/26562 | 6/1999 |
| WO | WO 99/59669 | 11/1999 |
| WO | WO 00/44319 | 8/2000 |
| WO | WO 01/54598 A1 | 8/2001 |
| WO | WO 03/057055 A1 | 7/2003 |
| WO | WO 2004/047689 A1 | 6/2004 |
| WO | WO 2004/047691 A1 | 6/2004 |
| WO | WO 2004/084768 A2 | 10/2004 |
| WO | WO 2004/110300 A2 | 12/2004 |
| WO | WO 2005/002474 A1 | 1/2005 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | WO 2007/034516 A1 | 3/2007 |
| WO | WO 2007/052975 A1 | 5/2007 |
| WO | WO 2009/083276 A1 | 7/2009 |
| WO | WO 2009/083583 A1 | 7/2009 |
| WO | WO 2009/098536 A1 | 8/2009 |

OTHER PUBLICATIONS

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, ppp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Duff, "Methyl Methacrylate in Spinal Stabilization," Techniques in Spinal Fusion and Stabilization, Hitchon et al., eds., 1995, pp. 147-151, Ch. 14, Thieme, New York.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.

Petrini et al., "Stabilizzazione Elastica," Patologia Degenerative del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrates Lombaires, Gastambide, ed., 1995, pp. 122-132, Expansion Scientifique Française, Paris, France.

Senegas, "La Ligamentoplastie Inter Vertébrate Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrate, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Preésentation à un an d'un dispositif amortissant d'assistance discale," 5èmes journées Avances & Controverses en pathologie rachidienne, Oct. 1-2, 1998, Faculte Libré de Medécine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

Kramer et al., "Interveterebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," SPINE, 1991, pp. S298-S301, vol. 16, No. 6, Supplement.

* cited by examiner

INTERCOSTAL SPACER DEVICE AND METHOD FOR USE IN CORRECTING A SPINAL DEFORMITY

This application is a divisional application of prior application Ser. No. 11/470,810, filed Sep. 7, 2006, which is incorporated herein by reference.

BACKGROUND OF THE INVENTION

The present invention relates generally to orthopaedic implants used for the correction of spinal deformities, and more specifically, but not exclusively, concerns apparatuses placed within the intercostal space of two ribs to allow for deformity correction or healing of the spinal column.

To secure and treat spinal deformities, including scoliosis, it is a generally accepted practice to place implants adjacent to or into the vertebrae to produce loads for correcting an abnormal curvature of the spine and to maintain appropriate vertebral support for the healing of the implanted bone fusion material.

Typical spinal implant systems are implanted through a posterior approach to the spinal column and utilize a rod as the support and stabilizing element connected to a series of two or more bone fasteners that have been inserted into two or more vertebrae. The connections between these components are then secured, thereby fixing a supporting construct to multiple levels in the spinal column.

SUMMARY OF THE INVENTION

Advancement of the state of orthopaedic implants and the treatment of pediatric and adolescent scoliosis is believed to be desirable. The present invention satisfies the need for improvements to the surgical treatment by providing a more mechanically efficient intercostal spacer device for implantation into multiple intercostal spaces of a patient's rib cage. The intercostal spacer device is a one piece construct fabricated from a biocompatible material. Alternatively, the intercostal spacer device may be a multiple piece construct that includes a flexible container that is fillable in situ to a desired amount, with a structure for at least part of the container providing shape control of the intercostal spacer device. An optional conduit coupled to the container allows for filling of the container, for example, by injecting a material into the container.

The present invention provides in one aspect, an intercostal spacer device. The intercostal spacer device includes a spacer member that has a superior end and an inferior end. Extending from both the superior end and inferior end are at least one pair of arms with a channel defined between each pair of arms. The spacer member is sized and configured to enable placement of the spacer member within an intercostal space, with each channel being sized to receive a rib allowing the intercostal spacer device to resist dislodgement from the ribs and produce a force for correcting a spinal deformity.

The present invention provides in another aspect, an intercostal spacer device that includes a flexible container for receiving an injectable material that is compressible following implantation between two adjacent ribs, wherein the flexible container is substantially impermeable to the injectable material. The intercostal spacer device further includes a conduit coupled to the flexible container for accepting the injectable material, and a structure for at least part of the flexible container when containing the material, wherein the structure has a shape to fit between two adjacent ribs.

Another aspect of the present invention provides a method of controlling at least part of the shape of the intercostal spacer device. The intercostal spacer device has a flexible container for containing an injectable material that is compressible following implantation, wherein the container is substantially impermeable to the injectable material. The intercostal spacer device further includes a structure for at least part of the flexible container. The method provides for creating the structure with at least one material for controlling at least part of the shape of the intercostal spacer device following implantation into the intercostal space.

The present invention provides in yet another aspect, an intercostal spacer system. The intercostal spacer system includes a plurality of intercostal spacer devices, with each of the intercostal spacer devices having a spacer member that has a superior end and an inferior end. Extending from both the superior end and inferior end are at least one pair of arms with a channel being defined between each pair of arms. The spacer member is sized and configured to enable placement of the member within an intercostal space, with each channel being sized to receive a rib, allowing the intercostal spacer device to resist dislodgement from the ribs when implanted. Following implantation, the plurality of intercostal spacer devices cooperate to dynamically produce a force for correcting a spinal deformity within a patient.

The present invention provides another aspect, a method of correcting a spinal deformity. The method includes the step of providing at least one intercostal spacer device, the intercostal spacer device includes a spacer member having first and second ends with at least one pair of arms extending from each of the first and second ends. The spacer member, the first pair of arms extending from the first end and the second pair of arms extending from the second end of the at least one intercostal spacer are sized for placement between a first rib and an adjacent second rib of a patient. The method further includes the positioning of the at least one intercostal spacer device into the intercostal space between the two adjacent ribs of the patient with the first rib disposed between the first pair of arms and the adjacent second rib disposed between the second pair of arms and thus securing the intercostal spacer device within the intercostal space and producing a force to correct the spinal deformity of the patient.

Another aspect of the present invention provides a method of correcting a spinal deformity. The method includes providing an intercostal spacer device, the intercostal spacer devices includes a flexible container for containing an injectable material that is compressible following implantation, wherein the flexible container is substantially impermeable to the injectable material. The intercostal spacer device further includes a conduit coupled to the flexible container for accepting the injectable material, and a structure for at least part of the flexible container when containing the material, wherein the structure has a shape of the intercostal spacer device that is sized and configured to fit between adjacent ribs in a patient. The method further includes implanting the intercostal spacer device between two adjacent ribs. The injectable material is then injected into the flexible container through the conduit such that the shape of the structure is achieved, thus producing a force to correct the spinal deformity of the patient.

Further, additional features and advantages are realized through the techniques of the present invention. Other embodiments and aspects of the invention are described in detail herein and are considered a part of the claimed invention.

DETAILED DESCRIPTION

Figure 1A:
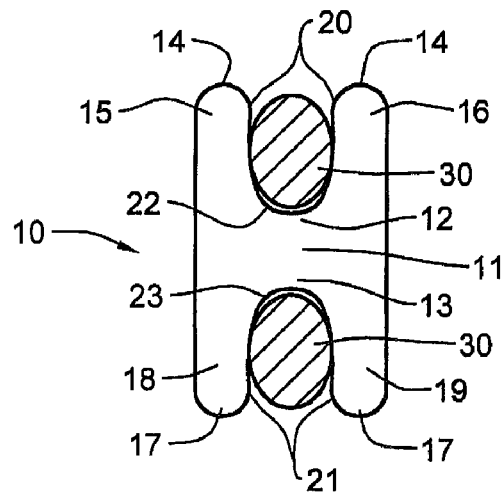
FIG. 1A is a side elevational view of one embodiment of an intercostal spacer device shown disposed between the cross-section of two adjacent ribs, in accordance with an aspect of the present invention.

As depicted in FIG. 1A, the general arrangement of an intercostal spacer device 10, in accordance with an aspect of the present invention, includes a spacer member 11 comprising a superior end 12 and an inferior end 13 with a central axis (not shown) extending between superior end 12 and inferior end 13. Extending in an upward direction from superior end 12 is preferably one pair of arms 14 that may include an anterior arm 15 and a posterior arm 16. Further, extending in a downward direction from inferior end 13 is preferably one pair of arms 17 that may include an anterior arm 18 and a posterior arm 19. Each pair of arms 14, 17 are integral to spacer member 11 and are sized to resist dislodgement of intercostal spacer device 10 following placement within the intercostal space. Further, each pair of arms 14, 17 are centered about the central axis of spacer member 11 resulting in a roughly H-shaped overall structure. An upper channel 20 is typically defined by a seat 22, anterior arm 15 and posterior arm 16. Additionally, a lower channel 21 is defined by a seat 23, anterior arm 18 and posterior arm 19. Anterior arm 15 and posterior arm 16 are disposed relatively parallel to each other and project in an upward manner from seat 22. Anterior arm 18 and posterior arm 19 project in a downward manner from seat 23 and are substantially parallel to each other. Each pair of arms 14, 17, together with seats 22, 23 form U-shaped channels 20, 21 respectively, which are each appropriately sized to receive a rib 30. When in use in the rib cage, intercostal spacer device 10 is placed within an intercostal space. Preferably, intercostal spacer device 10 is maneuvered in a manner allowing two adjacent ribs 30 to be positioned within channels 20, 21, causing the anterior aspect of the two adjacent ribs 30 to contact anterior arms 15, 18 and the posterior aspect of the two adjacent ribs 30 to contact posterior arms 16, 19.

Figure 1B:
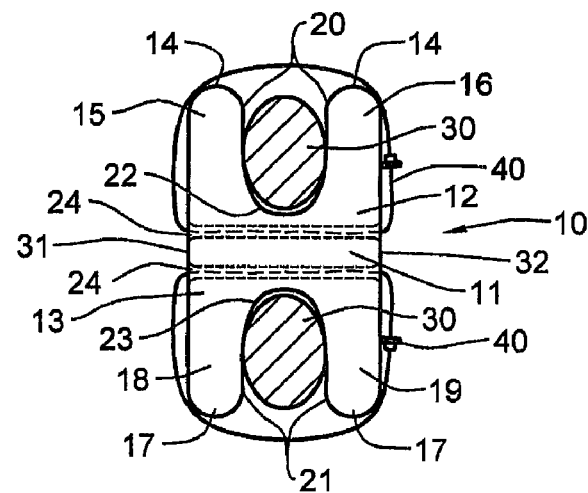
FIG. 1B is a side elevational view of one embodiment of an intercostal spacer device with two single connectors shown disposed between the cross-section of two adjacent ribs, in accordance with an aspect of the present invention.

With reference to FIGS. 1B, 1C, 1D, 1E and 1F, intercostal spacer device 10 includes a spacer member 11 comprising a superior end 12 and an inferior end 13. Extending in an upward direction from superior end 12 is preferably one pair of arms 14 that may include an anterior arm 15 and a posterior arm 16. Further, extending in a downward direction from inferior end 13 is preferably one pair of arms 17 that may include an anterior arm 18 and a posterior arm 19. An upper channel 20 is typically defined by a seat 22, anterior arm 15 and posterior arm 16. Additionally, a lower channel 21 is defined by a seat 23, anterior arm 18 and posterior arm 19. Each pair of arms 14, 17 together with seats 22, 23 form U-shaped channels 20, 21 respectively, which are each appropriately sized to receive a rib 30. Typically, at least one through hole 24 is directed in the anterior to posterior direction and located within spacer member 11 in the intercostal spacer device 10. In one approach, connector 40 (see FIG. 1B) is inserted into hole 24 following the placement of intercostal spacer device 10 between adjacent ribs 30. As depicted in FIG. 1B, a first connector 40 may be inserted through passage or hole 24 that extends from an anterior surface 31 of spacer member 11 to a posterior surface 32 of spacer member and then wraps over the superior surface of rib 30 which is positioned within upper channel 20. A second connector 40 may be inserted through a second passage or hole 24 that extends from anterior surface 31 of spacer member 11 to posterior surface 32 of spacer member 11 and then wraps over the inferior surface of a second adjacent rib 30 which is positioned within lower channel 21. The ends of connectors 40 may be secured using crimps, knots, ties or other suitable fasteners. It is understood to those skilled in the art that other securement techniques and configurations are contemplated and will depend on the type of connector 40 used within intercostal spacer device 10.

Figure 1C:
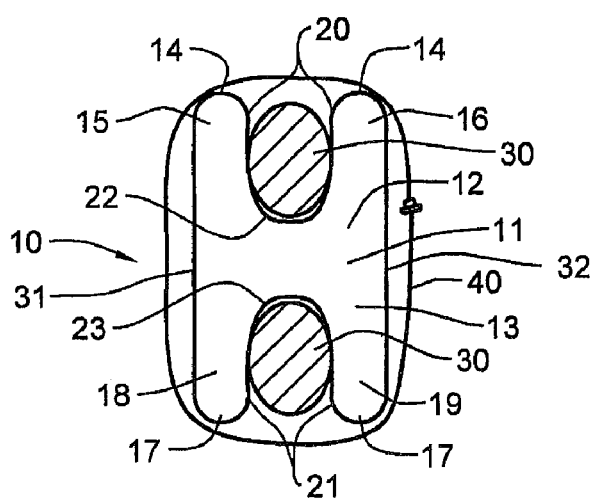
FIG. 1C is a side elevational view of one embodiment of an intercostal spacer device shown disposed between the cross-section of two adjacent ribs, with a single connector surrounding the entire intercostal spacer device, in accordance with an aspect of the present invention.

As shown in FIG. 1C, an alternative method of securing intercostal spacer device 10 within the intercostal space may include extending at least one connector 40 around the circumference of the exterior surface of intercostal spacer device 10 and the two adjacent ribs 30. The ends of connector 40 may be then be secured using crimps, knots, ties or other suitable fasteners, although it is understood to those skilled in the art that other securement techniques and configurations are contemplated and will depend on the type of connector 40 used in securing intercostal spacer device 10 within the intercostal space.

Figure 1D:
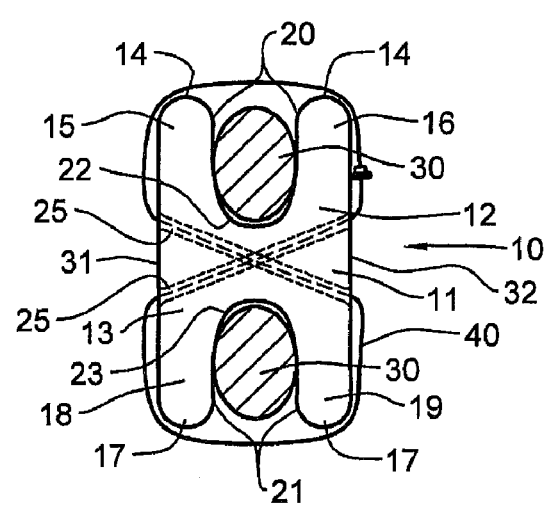
FIG. 1D is a side elevational view of one embodiment of an intercostal spacer device, shown disposed between the cross-section of two adjacent ribs, with a single connector utilizing an alternative securing configuration, in accordance with an aspect of the present invention.

As seen in FIG. 1D, another alternative method of securing intercostal spacer device 10 within the intercostal space is contemplated. FIG. 1D depicts the use of at least one connector 40 typically utilizing a figure-8 configuration. A single or multiple connector 40 may be inserted through an angled passage or hole 25 that extends from anterior surface 31 of spacer member 11 to posterior surface 32 of spacer member 11 and then looped over the superior surface of rib 30 which is positioned within upper channel 20. Connector 40 is further passed through a second angled passage or hole 25 that extends from anterior surface 31 of spacer member 11 to posterior surface 32 of spacer member allowing connector 40 to also loop over the inferior surface of a second adjacent rib 30 which is positioned within lower channel 21. The two ends of connector 40 may be secured using crimps, knots, ties or other suitable fastener. It is understood to those skilled in the art that other securement techniques and configurations are contemplated and will depend on the type of connector 40 used within intercostal spacer device 10. Connector 40 may be in the form of a wire, cable, tether, belt, band, cord or other suitable structure for securement within the intercostal space and may be fabricated from a material selected from the group consisting of carbon fiber composite polymers, bio-compatible metals, resorbable polymers, bio-inert polymeric materials, and any combinations of these materials.

Figure 1E:
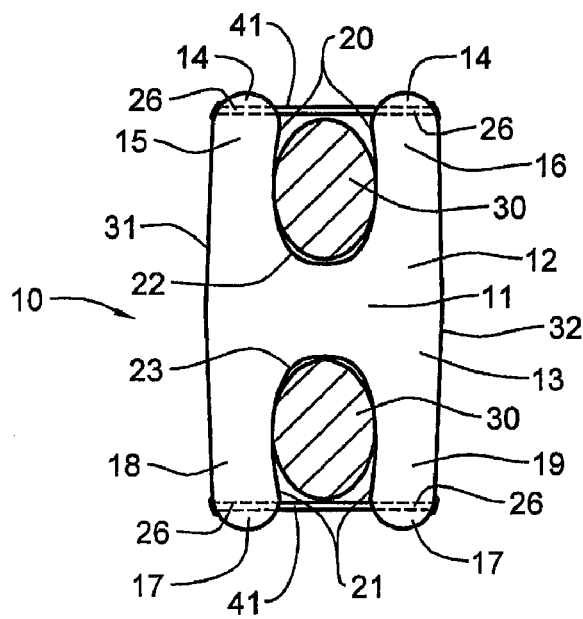
FIG. 1E is a side elevational view of one embodiment of an intercostal spacer device shown disposed between the cross-section of two adjacent ribs, with two alternative single connectors inserted through two bore holes, in accordance with an aspect of the present invention.
Figure 1F:
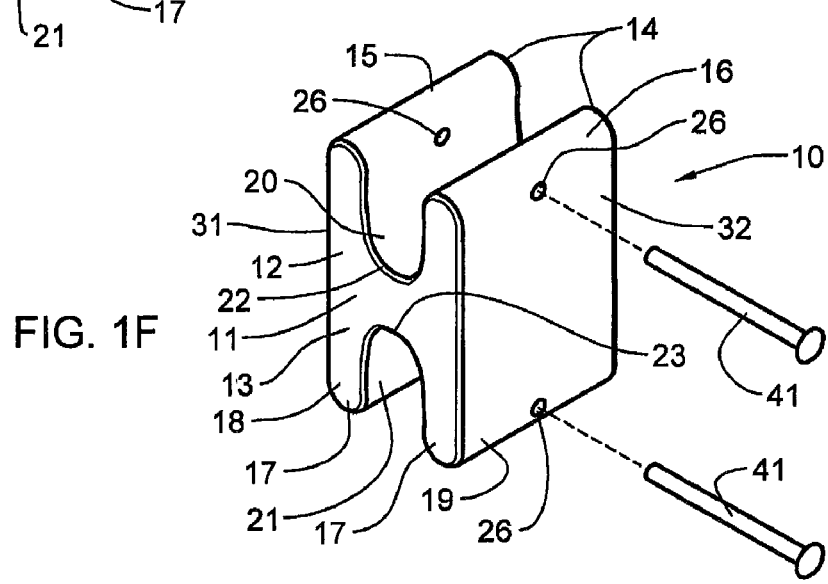
FIG. 1F is a perspective view of the intercostal spacer device embodiment of FIG. 1E with the two alternative single connectors extracted from the two bore holes, in accordance with an aspect of the present invention.

Another alternative method for securing intercostal spacer device 10 within the intercostal space is seen at FIGS. 1E and 1F. As shown, intercostal spacer device 10 includes a spacer member 11 comprising a superior end 12 and an inferior end 13. Extending in an upward direction from superior end 12 is preferably one pair of arms 14, including anterior arm 15 and posterior arm 16. Further, extending in a downward direction from inferior end 13 is preferably one pair of arms 17 that may include anterior arm 18 and posterior arm 19. As provided above, upper channel 20 is typically defined by seat 22, anterior arm 15 and posterior arm 16. Additionally, lower channel 21 is defined by seat 23, anterior arm 18 and posterior arm 19. Each pair of arms 14, 17 together with seats 22, 23 form U-shaped channels 20, 21 respectively, which are each appropriately sized to receive a rib 30. Preferably, at least one through hole 26 is directed in an anterior to posterior direction and passes through anterior arms 15, 18 and posterior arms 16, 19 located within superior pair of arms 14 and inferior pair of arms 17, respectively. As seen in FIG. 1E, at least one hole 26 extends through superior pair of arms 14 and is substantially parallel to a second hole 26 extending through inferior pair of arms 17. In use, intercostal spacer device 10 is placed within an intercostal space and typically is maneuvered in a manner to allow two adjacent ribs 30 to be positioned within upper and lower channels 20, 21, causing the anterior aspect of two adjacent ribs 30 to contact anterior arms 15, 18 and the posterior aspect of two adjacent ribs 30 to contact posterior arms 16, 19. Following final placement of intercostal spacer device 10, a connector 41 (see FIG. 1F) is inserted into hole 26 following the placement of intercostal spacer device 10 between adjacent ribs 30. As depicted in FIG. 1E, one connector 41 may be inserted through hole 26 that is located in the most upper portion of superior pair of arms 14 and span upper channel 20 and across the superior margin of rib 30. Preferably, a second connector 41 is inserted through a second hole 26 located in the most downward portion of inferior set of arms 17 and span lower channel 21 and across the inferior margin of rib 30. The ends of the two connectors 41 may be secured using crimps, caps, nuts, rivets, or other suitable fastener device. It is understood to those skilled in the art that other securement techniques and configurations are contemplated and will depend on the type of connector 41 used within intercostal spacer device 10. Connector 41 may be in the form of a bolt, screw, lock pin, rivet, staple, press-fit pin or other suitable structure for securement within the intercostal space and may be fabricated from a material selected from the group consisting of carbon fiber composite polymers, bio-compatible metals, resorbable polymers, bio-inert polymeric materials, and any combinations of these materials.

Figure 2:
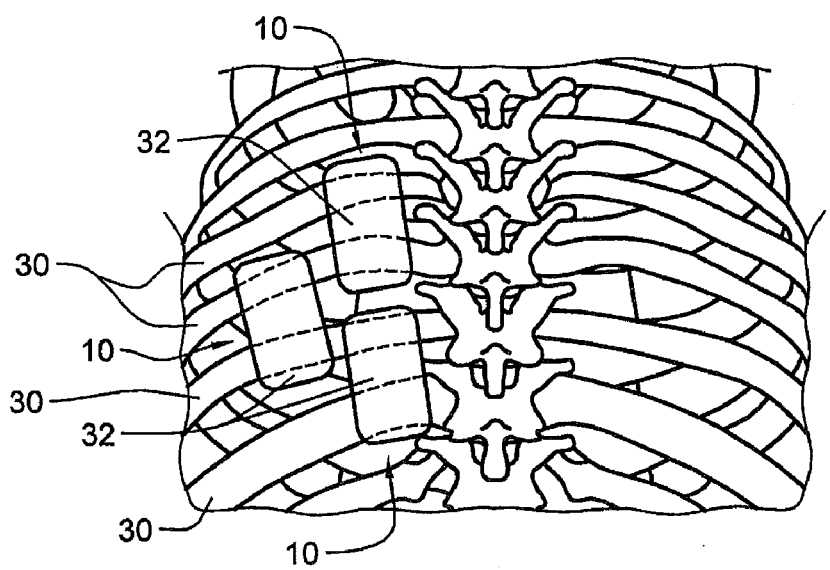
FIG. 2 is a posterior elevational view of one embodiment of an intercostal spacer system implanted in the posterior aspect of the rib cage, in accordance with an aspect of the present invention.

FIG. 2 depicts an intercostal spacer system that includes a plurality of intercostal spacer devices 10 placed within the rib cage to correct a spinal deformity of a patient. Multiple intercostal spacer devices 10 are inserted into the intercostal spaces of several adjacent ribs 30 at corresponding deformed spinal levels. Adjacent intercostal spacer devices 10 are preferably implanted in an offset manner relative to each other, resulting in an overall generally staggered arrangement. As described previously, each of the plurality of intercostal spacer devices 10 may be secured within the intercostal space with at least one connector 40, 41 (not shown). Alternatively, at least one connector 40 may link or couple each of the plurality of intercostal spacer devices 10 to each other (not shown). Typically, the number of intercostal spacer devices 10 implanted may be dependent upon the severity of the spinal deformity and the affected levels of the spinal column. By way of example only, in FIG. 2, three intercostal spacer devices 10 are placed on the concave side of a medial-lateral deformity that spans four levels of the spinal column.

Figure 3:
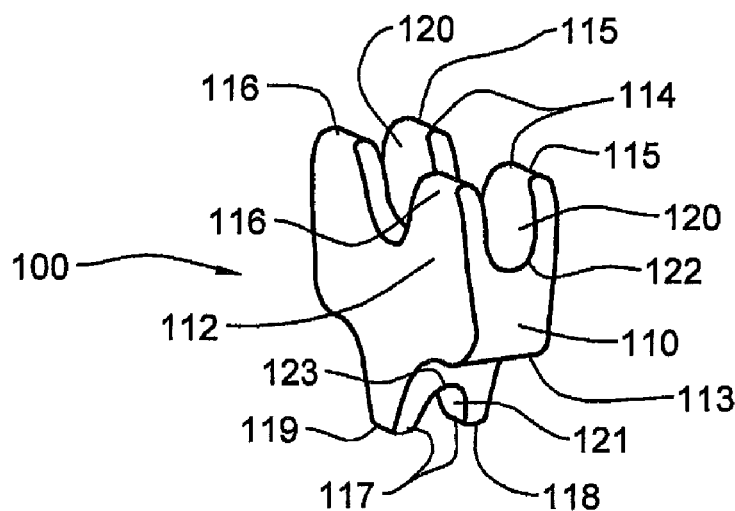
FIG. 3 is a perspective view of one embodiment of an intercostal spacer device, in accordance with an aspect of the present invention.

FIG. 3 depicts an alternative embodiment of an intercostal spacer device 100. Intercostal spacer device 100 includes a spacer member 110 comprising of a superior end 112 and an inferior end 113 with a central axis (not shown) extending between superior end 112 and inferior end 113. Extending in an upward direction from superior end 112 is preferably two pair of arms 114, with each pair of arms including an anterior arm 115 and a posterior arm 116. Further, extending from inferior end 113 in a downward direction is preferably one pair of arms 117 that may include an anterior arm 118 and a posterior arm 119. Each pair of arms 114, 117 are integral to spacer member 110 usually with one of the two superior pair of arms 114 being offset laterally relative to the central axis and the second of the two superior pair of arms 114 being offset medially relative to the central axis. The inferior pair of arms 117 are preferably centered about the central axis resulting in a roughly Y-shaped overall structure defining intercostal spacer device 100. For each of superior pair of arms 114, an upper channel 120 is typically defined by a seat 122, anterior arm 115 and posterior arm 116. Additionally, for inferior pair of arms 117, a lower channel 121 is defined by a seat 123, anterior arm 118 and posterior arm 119. For both superior pair of arms 114, anterior arm 115 and posterior arm 116 are disposed relatively parallel to each other and project in a generally upward manner from seat 122. For inferior pair of arms 117, anterior arm 118 and posterior arm 119 project in a generally downward manner from seat 123 and are substantially parallel to each other. Each pair of arms 114, 117, together with seats 122, 123 form U-shaped channels 120, 121 respectively, which are each appropriately sized to receive a rib 30 and allow intercostal spacer device 100 to resist dislodgement following implantation within the rib cage.

Although not shown, it is contemplated that either connector 40, 41 may be utilized with intercostal spacer device 100 to secure intercostal spacer device 100 within an intercostal space. As described above, it is contemplated that connector 40 may pass through anterior to posterior directed, single or multiple, straight or angled holes or passages (not shown) within spacer member 110, thereby allowing connector 40 to wrap or loop around or over both superior pair of arms 114 and inferior pair of arms 117 allowing for securement of intercostal spacer device 100 within the intercostal space in the same or similar manner as described above for intercostal spacer device 10. Further, as discussed above, it is understood that connector 41 may be inserted through anterior to posterior directed, single or multiple straight holes or passages (not shown) within both superior pair of arms 114 and inferior pair of arms 117. The holes located in both superior pair of arms 114 being substantially parallel to the hole or passage located in inferior pair of arms 117. When in use, connector 41 preferably will be inserted through the holes that are located in the upper most portion of both superior pair of arms 114 and span each upper channel 120 and across the superior margin of rib 30. Additionally, a second connector 41 may be inserted through a hole or passage located in the downward most portion of inferior set of arms 117 and span lower channel 121 crossing over the inferior margin of rib 30.

Figure 4A:
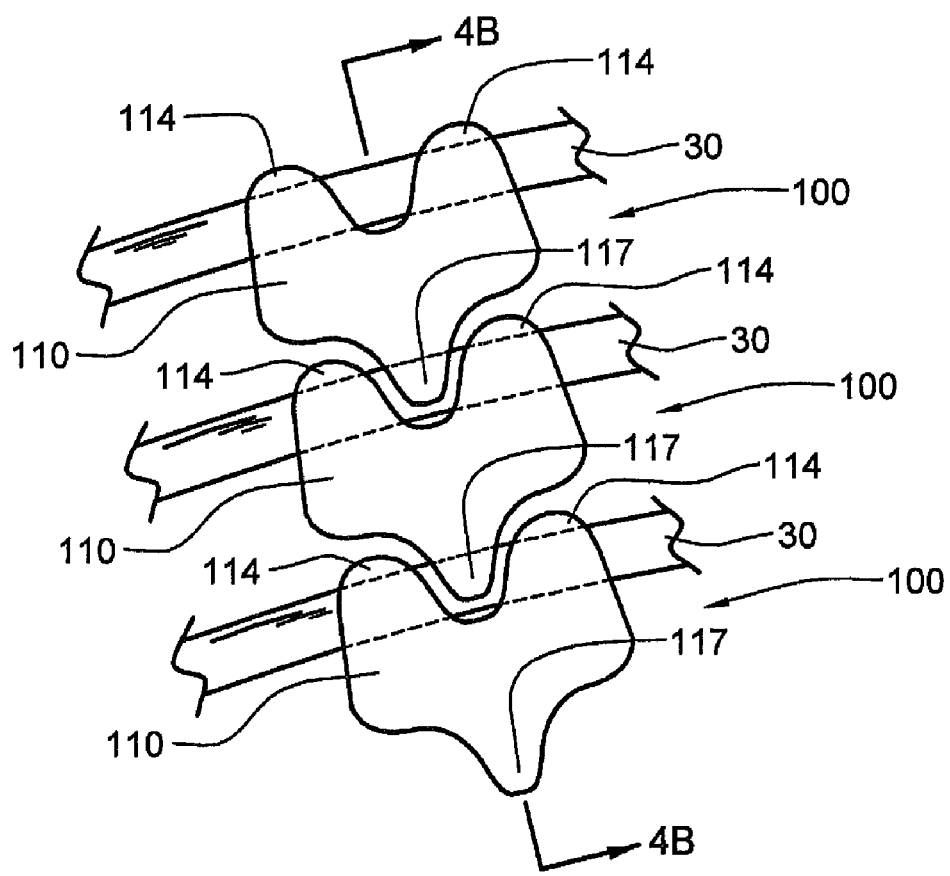
FIG. 4A is a posterior elevational view of one embodiment of an intercostal spacer system shown disposed between three ribs, in accordance with an aspect of the present invention.
Figure 4B:
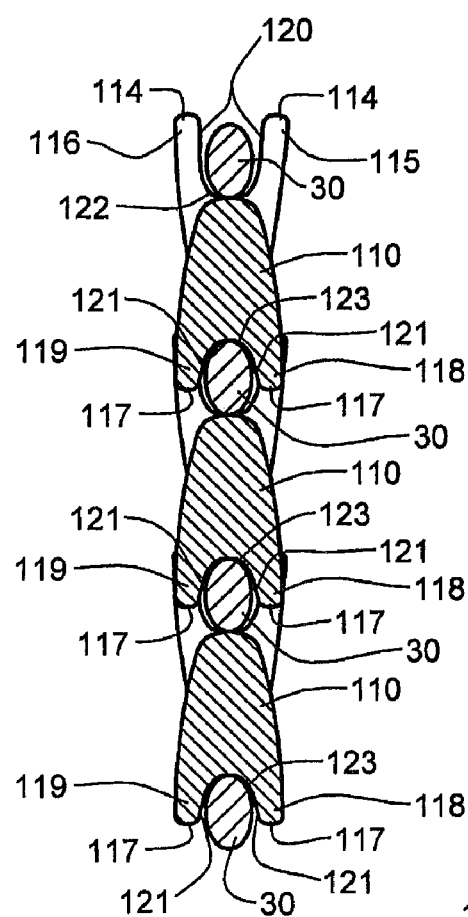
FIG. 4B is a cross-section side elevational view of the intercostal spacer device system of FIG. 4A taken along line 4B-4B shown disposed between the cross-section of four adjacent ribs, in accordance with an aspect of the present invention.
Figure 4C:
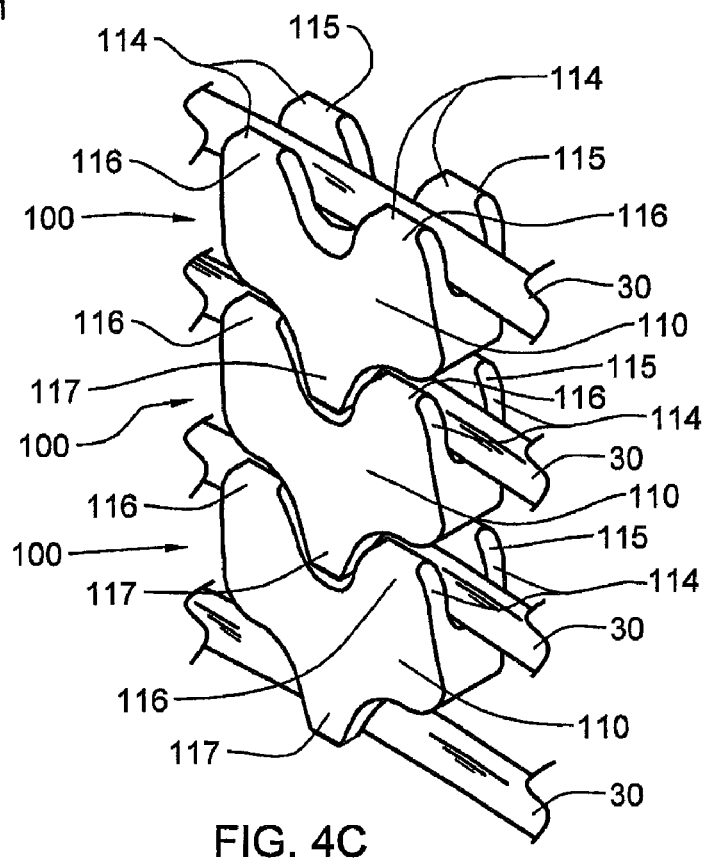
FIG. 4C is a posterior perspective view of one embodiment of an intercostal spacer system shown disposed between four adjacent ribs, in accordance with an aspect of the present invention.

As shown in FIGS. 4A, 4B and 4C, when used in the rib cage, intercostal spacer device 100 is typically placed within an intercostal space. Preferably, intercostal spacer device 100 is maneuvered in a manner allowing two adjacent ribs 30 to be positioned within two upper channels 120 and lower channel 121, causing the anterior aspect of two adjacent ribs 30 to contact anterior arms 115, 118 and the posterior aspect of two adjacent ribs 30 to contact posterior arms 116, 119.

FIGS. 4A and 4B further depict an alternative embodiment of an intercostal spacer system that includes a plurality of intercostal spacer devices 100 in use within the rib cage to correct a spinal deformity of a patient. Multiple intercostal spacer devices 100 are inserted into the intercostal spaces of adjacent ribs 30 at corresponding affected spinal levels. Adjacent intercostal spacer devices 100 are preferably implanted in close association relative to each other, resulting in an overall generally linear arrangement of the system as shown in FIG. 4A. Preferably, when implanted, the shape and size of intercostal spacer device 100 allows for inferior pair of arms 117 of an upper placed intercostal spacer device 100 to be positioned proximate or within the space defined between the two superior pair of arms 114 of an adjacent lower placed intercostal spacer device 100. As described previously, each of the plurality of intercostal spacer devices 100 may be secured within the intercostal space with at least one connector 40, 41 (not shown). Alternatively, at least one connector 40 may link or couple each of the plurality of intercostal spacer devices 100 to each other (not shown). Typically, the number of intercostal spacer devices 100 implanted is dependent upon the severity of the spinal deformity and the affected levels of the spinal column. By way of example only, in FIG. 4C, three intercostal spacer devices 100 are shown to be used to correct a spinal deformity that spans four levels of the spinal column.

Figure 5:
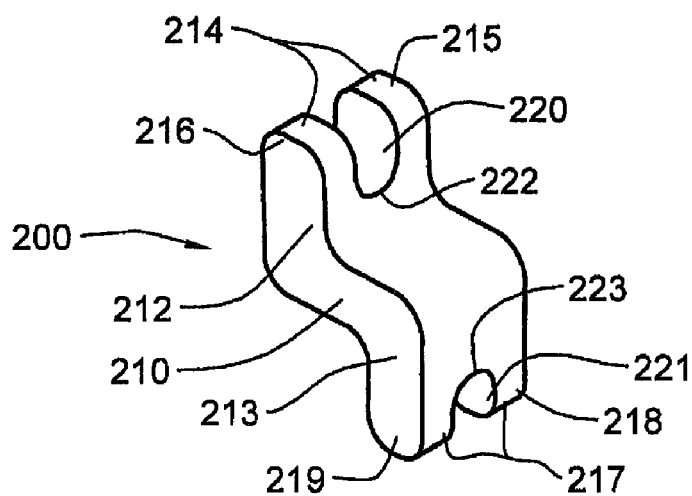
FIG. 5 is a perspective view of one embodiment of an intercostal spacer device, in accordance with an aspect of the present invention.

FIG. 5 depicts still another alternative embodiment of an intercostal spacer device 200. Intercostal spacer device 200 includes a spacer member 210 comprising a superior end 212 and an inferior end 213 with a central axis (not shown) extending between superior end 212 and inferior end 213. Extending in an upward direction from superior end 212 is preferably one pair of arms 214 including an anterior arm 215 and a posterior arm 216. Further, extending in a downward direction from inferior end 213 is preferably one pair of arms 217 that may include an anterior arm 218 and a posterior arm 219. Each pair of arms 214, 217 are integral to spacer member 210 usually with superior pair of arms 214 being offset laterally relative to the central axis and inferior pair of arms 217 being preferably offset medially relative to the central axis. It is contemplated, that an alternative configuration of intercostal spacer device 200 may include each pair of arms 214, 217 to be opposite as described previously, in that superior pair of arms 214 being offset medially relative to the central axis and inferior pair of arms 217 being offset laterally relative to the central axis. An upper channel 220 is typically defined by a seat 222, anterior arm 215 and posterior arm 216. Additionally, for inferior pair of arms 217, a lower channel 221 is defined by a seat 223, anterior arm 218 and posterior arm 219. Anterior arm 215 and posterior arm 216 are disposed relatively parallel to each other and project in a generally upward direction from seat 222. Inferior pair of arms 217, anterior arm 218 and posterior arm 219 project in a generally downward direction from seat 223 and are substantially parallel to each other. Each pair of arms 214, 217, together with seats 222, 223 form U-shaped channels 220, 221 respectively, which are each appropriately sized to receive a rib 30.

Although not shown, as discussed above, it is contemplated that either connector 40, 41 may be utilized with intercostal spacer device 200 to secure intercostal spacer device 200 within an intercostal space. As described previously, it is contemplated that connector 40 may be positioned through anterior to posterior directed, single or multiple, straight or angled holes (not shown) within spacer member 210, thereby allowing connector 40 to wrap or loop around or over superior pair of arms 214 and inferior pair of arms 217 allowing for securement of intercostal spacer device 200 within the intercostal space in the same or similar manner as described for intercostal spacer device 10. Further, as discussed above, it is understood that connector 41 may be inserted through anterior to posterior directed, single or multiple straight holes or passages (not shown) within superior pair of arms 214 and inferior pair of arms 217. The hole or passage located in superior pair of arms 214 being substantially parallel to the hole located in inferior pair of arms 217. When in use, connector 41 preferably will be inserted through the hole or passage that is located in the upper most portion of superior pair of arms 214 and span upper channel 220 and across the superior margin of rib 30. Additionally, a second connector 41 may be inserted through a hole or passage located in the downward most portion of inferior set of arms 217 and span lower channel 221 and across the inferior margin of rib 30.

Figure 6:
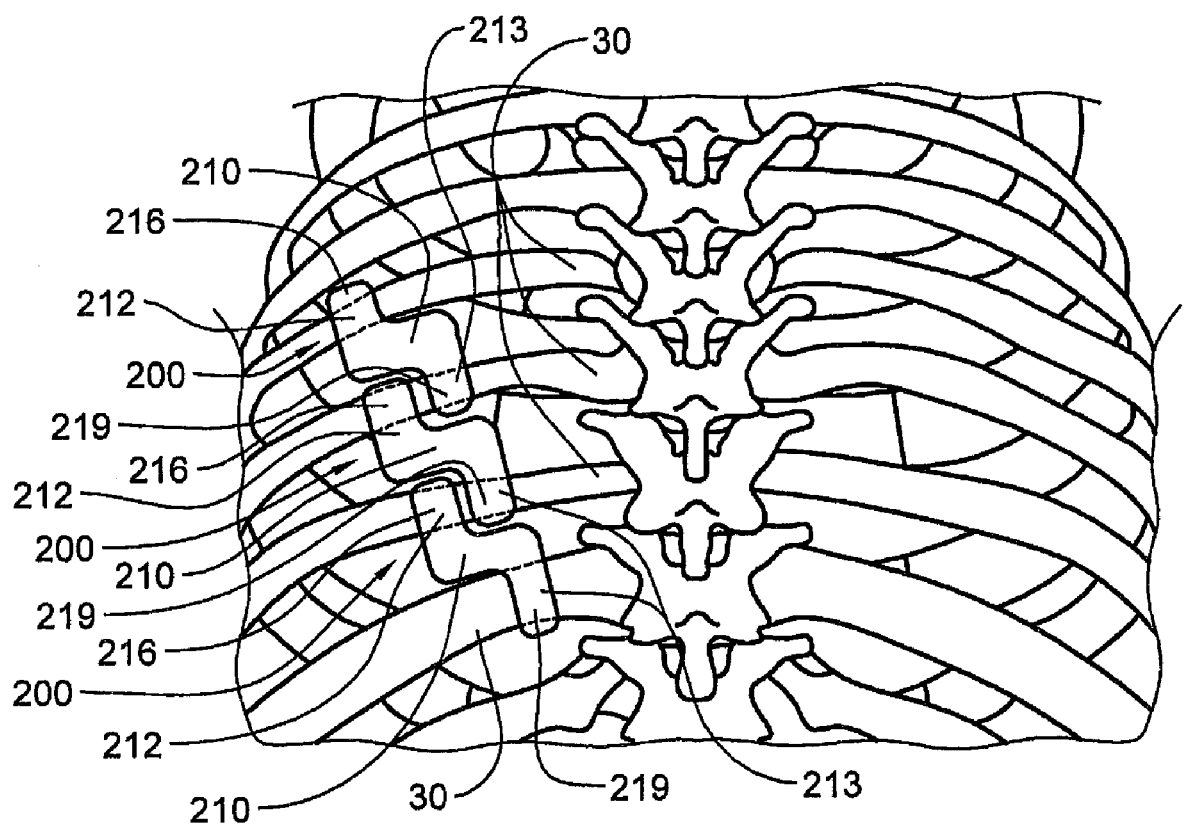
FIG. 6 is a posterior elevational view of one embodiment of an intercostal spacer system implanted in the posterior aspect of the rib cage, in accordance with an aspect of the present invention.
Figure 7:
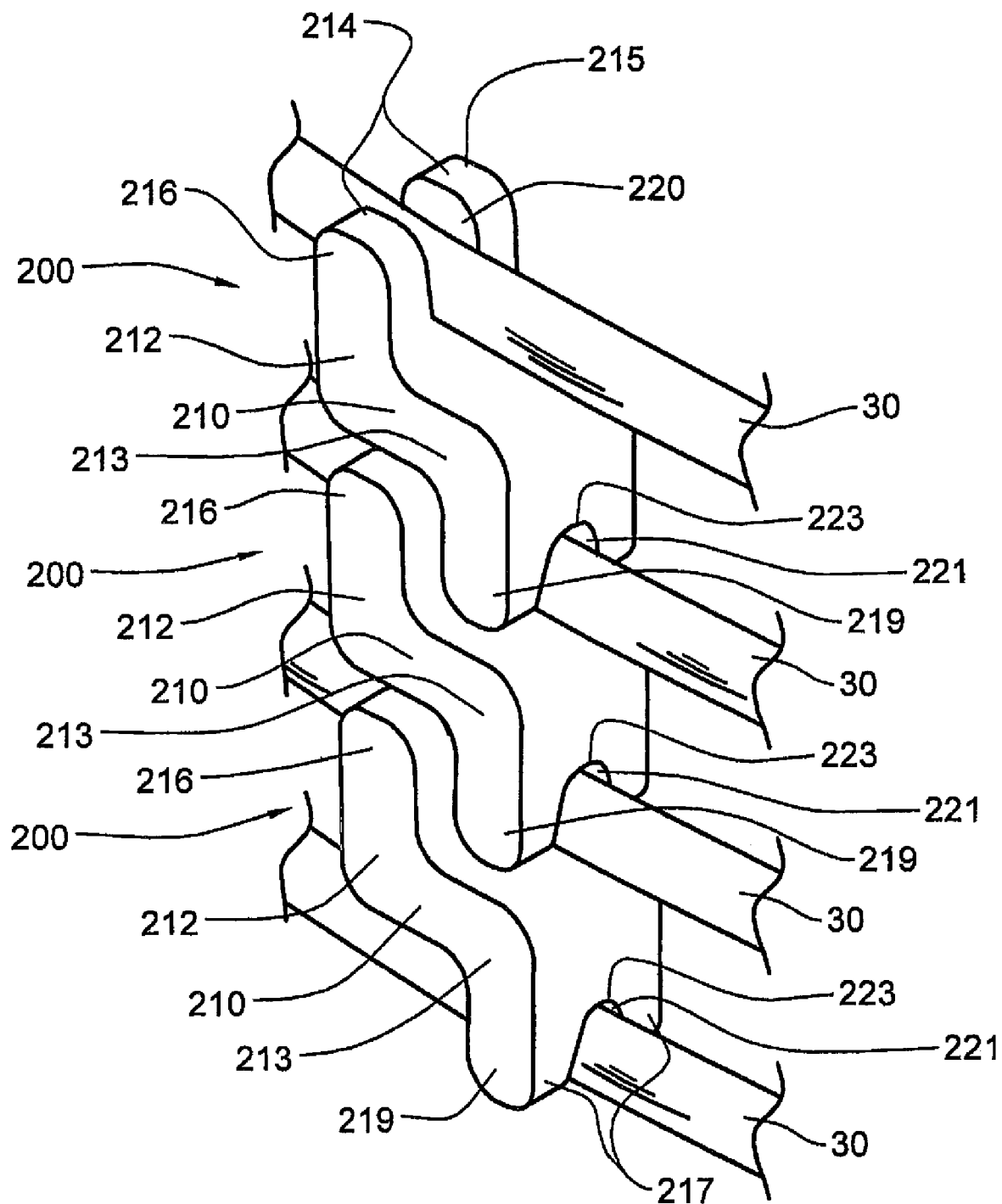
FIG. 7 is a posterior elevational view of one embodiment of an intercostal spacer device system shown disposed between four adjacent ribs, in accordance with an aspect of the present invention.

As shown in FIGS. 6 and 7, when used in the rib cage, intercostal spacer device 200 is placed within an intercostal space. Preferably, intercostal spacer device 200 is maneuvered in a manner allowing two adjacent ribs 30 to be positioned within each of the upper channel 220 and lower channel 221, causing the anterior aspect of two adjacent ribs 30 to contact anterior arms 215, 218 and the posterior aspect of two adjacent ribs 30 to contact posterior arms 216, 219. Upper channel 220 and lower channel 221 are sized and configured to provide resistance to any in vivo forces that may dislodge intercostal spacer device 200 from its position within the intercostal space.

FIGS. 6 and 7 further depict an alternative embodiment of an intercostal spacer system which includes a plurality of intercostal spacer devices 200 in use within the rib cage to correct a spinal deformity of a patient. Multiple intercostal spacer devices 200 are inserted into the intercostal spaces of adjacent ribs 30 at corresponding affected spinal levels. Adjacent intercostal spacer devices 200 are preferably implanted in close approximation relative to each other, resulting in an overall generally linear arrangement of the system. Preferably, when implanted, the shape and size of intercostal spacer device 200 allows for inferior pair of arms 217 of an upper intercostal spacer device 200 to either contact or be proximate to spacer member 210 of the adjacent and lower intercostal spacer device 200. Additionally, when implanted, typically, superior pair of arms 214 of lower intercostal spacer device 200 will contact or be in close approximation to spacer member 210 of adjacent upper intercostal spacer device 200. As shown in FIG. 7, following implantation, rib 30 may be simultaneously located within lower channel 221 of a superior placed intercostal spacer device 200 and upper channel 220 of an inferior placed intercostal spacer device 200. As described previously, each of the plurality of intercostal spacer devices 200 may be secured within the intercostal space with at least one connector 40, 41 (not shown). Alternatively, at least one connector 40 may link or couple each of the plurality of intercostal spacer devices 200 to each other (not shown). Usually, the number of intercostal spacer devices 200 implanted is dependent upon the severity of the spinal deformity and the affected levels of the spinal column. By way of example only, in FIG. 6, three intercostal spacer devices 200 are used to correct a spinal deformity that spans four levels of the spinal column.

With respect to the various embodiments of the intercostal spacer device 10, 100, 200 described herein, the intercostal spacer device 10, 100, 200 can be fabricated from materials that are flexible or exhibit at least some flexibility. Additionally, the intercostal spacer device 10, 100, 200 may be fabricated from materials that are resilient and/or elastic, so it can assume various shapes during and after insertion and securement within the intercostal space.

The intercostal spacer device 10, 100, 200 can be made from any biocompatible material, material of synthetic or natural origin, and material of a resorbable or non-resorbable nature. Suitable examples of construct material include resorbable materials including polylactide, polyglycolide, tyrosine-derived polycarbonate, polyanhydride, polyorthoester, polyphosphazene, calcium phosphate, hydroxyapatite, bioactive glass, collagen, albumin, fibrinogen and combinations thereof; and non-resorbable materials including polyethylene, polyester, polyvinyl alcohol, polyacrylonitrile, polyamide, polytetrafluorethylene, poly-praraphenylene terephthalamide, polyetheretherkeone, poly urethane, and combinations thereof. Further non-resorbable materials may include carbon-reinforced polymer composites, shape-memory alloys, titanium, titanium alloys, cobalt chrome alloys, stainless steel, and combinations thereof. The intercostal spacer device 10, 100, 200 is preferably fabricated from material capable of resisting compressive motion (or loads) with a stiffness of about 10 to about 300 N/mm (newtons per millimeter).

The method for correcting a spinal deformity includes, providing at least one intercostal spacer device 10, intercostal spacer device 10 includes spacer member 11 comprising superior end 12 and inferior end 13 with a central axis (not shown) extending between superior end 12 and inferior end 13. Extending outward from superior end 12 is preferably at least one superior pair of arms 14 that may include anterior arm 15 and posterior arm 16. Further, extending outward from inferior end 13 is preferably one superior pair of arms 17 that may include anterior arm 18 and posterior arm 19. Each pair of arms 14, 17 are integral to spacer member 11. An upper channel 20 is typically defined by seat 22, anterior arm 15 and posterior arm 16. Additionally, a lower channel 21 is defined by seat 23, anterior arm 18 and posterior arm 19. Each pair of arms 14, 17, together with seats 22, 23 form U-shaped channels 20, 21 which are each appropriately sized to receive a rib 30. The method further includes preferably positioning intercostal spacer device 10 within the intercostal space between two adjacent ribs 30. Preferably, the intercostal spacer device 10 is maneuvered in a manner that typically results in the positioning of a first rib 30 into upper channel 20 between superior pair of arms 14 and a second rib 30 into lower channel 21 between inferior pair of arms 17. Placement of ribs 30 within upper and lower channels 20, 21 secures intercostal spacer device 10 within the patient's rib cage and produces a compressive or distraction force, depending on the spinal curvature geometry, for correcting a spinal deformity. It is further understood that the method may include inserting connectors 40, 41 into each of the intercostal spacer devices 10 following implantation into the intercostal space. Preferably, at least one connector 40 may be utilized with each individual intercostal spacer device 10 or alternatively, at least one connector 40 may link or couple the plurality of intercostal spacer devices to each other. It is contemplated herein that the steps of the method for connecting a spinal deformity are analogous to those that may be used with intercostal spacer device 100 and intercostal spacer device 200 described herein.

FIGS. 8, 9, 10 and 11 show a further alternative embodiment of the intercostal spacer device 400 that can be formed in situ during a surgical procedure. Intercostal spacer device 400 includes the following basic aspects: a flexible container 402 and a structure 404 for at least part of flexible container 402 that controls at least part of the shape of intercostal spacer device 400. Flexible container 402 can be filled or injected through optional conduit 406 after placement. Further, structure 404 may be folded or otherwise reduced in size prior to use in some aspects. Together with an unfilled container 402, in some aspects, intercostal spacer device 400 can create a smaller footprint during implantation. Once filled, structure 404 provides support and containment for the flexible container 402, as well as providing shape control for at least part of intercostal spacer device 400.

Figure 8:
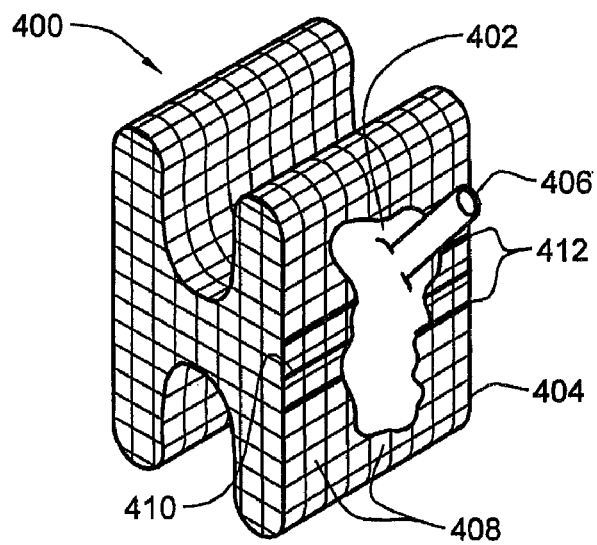
FIG. 8 is a perspective partial cut-away view of one embodiment of an unfilled intercostal spacer device with the container in the structure, in accordance with an aspect of the present invention.

FIG. 8 depicts a partially cut-away view of intercostal spacer device 400. As shown in FIG. 8, intercostal spacer device 400 comprises an unfilled flexible container 402 inside structure 404. Preferably, flexible container 402 is in an evacuated state during implantation and prior to being filled. Where a valve (e.g., a one-way valve) is coupled to flexible container 402, with flexible container 402 preferably being evacuated prior to or during the process of coupling the valve thereto. In this embodiment, structure 404 is outside flexible container 402. However, as will be described in more detail below, flexible container 402 can be outside structure 404, or flexible container 402 and structure 404 can be integrated. In addition, although structure 404 is shown to be roughly H-shaped to fit between adjacent ribs 30, structure 404 may have any shape necessary for the particular surgical application. For example, structure 404 could instead have a roughly cylindrical shape to replace an intervertebral disc. As another example, structure 404 could be spherically or elliptically shaped to replace part of the intervertebral disc, for example, the nucleus pulpous, leaving the rest of the disc intact. Further, although structure 404 is shown enveloping the flexible container 402, structure 404 could be for only a portion of flexible container 402, depending on the particular application. For example, it may be desired to prevent bulging of flexible container 402 only in a particular area. Coupled to flexible container 402 is optional conduit 406 for accepting a material that is compressible following implantation. Structure 404 provides support for and containment of flexible container 402, when filled.

Flexible container 402 is flexible and substantially impermeable to the material it will be filled with. However, depending on the application, flexible container 402 may be permeable to other materials, for example, it may be air and/or water permeable. In the present example, flexible container 402 takes the form of a bag or balloon, but can take other forms, so long as flexible and substantially impermeable to the material it will be filled with. Thus, flexible container 402 must be substantially impermeable to the injectable material, for example, in a liquid state during filling and prior to curing. Examples of container materials include silicone, rubber, polyurethane, polyethylene terephthalate (PET), polyolefin, polycarbonate urethane, and silicone copolymers.

Conduit 406 accepts the injectable material being used to fill flexible container 402. Preferably, conduit 406 comprises a one-way valve, however, a two-way valve is also contemplated, as another example. Conduit 406 can comprise any material suitable for implanting, for example, various plastics. Also preferably, conduit 406 is constructed to be used with a delivery system for filling flexible container 402, such as, for example, a pressurized syringe-type delivery system. However, the delivery system itself forms no part of the present invention. It is contemplated that, conduit 406 may be optional. Other examples of how to fill flexible container 402 comprise the use of a self-sealing material for flexible container 402, or leaving an opening in flexible container 402 that is closed (e.g., sewn shut) intraoperatively after filling. Using a curable material to fill flexible container 402 may also serve to self-seal flexible container 402.

In use, flexible container 402 is filled with an injectable material that is compressible following implantation between two adjacent ribs of a patient. The compressibility characteristic ensures that the injected material exhibits viscoelastic behavior and that, along with structure 404, the intercostal spacer device 400 can accept compressive loads. Preferably, intercostal spacer device 400 may be capable of resisting compressive motion (or loads) with a stiffness of about 10 to about 300 N/mm (newtons per millimeter). The material is preferably injectable, and may be compressible immediately or after a time, for example, after curing. For purposes of the invention, the compressibility characteristic is necessary during end use, i.e., after implantation. Materials that could be used include, for example, a plurality of beads (e.g., polymer beads) that in the aggregate are compressible, or materials that change state from exhibiting fluid properties to exhibiting properties of a solid or semi-solid. Examples of such state-changing materials include two-part curing polymers and adhesive, for example, platinum-catalyzed silicone, epoxy or polyurethane.

As noted above, structure 404 provides support for and containment of container 402 when filled, as well as at least partial shape control of intercostal spacer device 400. Structure 404 comprises, for example, a structural mesh comprising a plurality of fibers and/or wires 408. Within the structural mesh are shape-control fibers and/or wires 410. In one example, shape control is provided by wires of a shape-memory alloy (e.g., Nitinol). Shape-memory alloy wire(s) 410 can be coupled to the structural mesh (inside or outside), or weaved into the mesh (i.e., integrated). Coupling can be achieved, for example, by stitching, twisting, or closing the wire on itself. Alternatively, shape control can be provided by other wires or fibers that do not "give" in a particular direction, for example, metal or metal alloys (e.g., tantalum, titanium or steel, and non-metals, for example, carbon fiber, PET, polyethylene, polypropylene, etc.). The shape-memory alloy can be passive (e.g., elastic) or active (e.g., body-temperature activated). The use of metal, metal alloy or barium coated wires or fibers can also improve radiopacity for imaging. The remainder of structure 404 can take the form of, for example, a fabric jacket, as shown in FIG. 8. Although the shape-memory alloy wires 410 make up only a portion of the structural mesh of FIG. 8, it will be understood that there could be more such wires, up to and including comprising the entirety of the mesh. The fabric jacket in this example contains and helps protect flexible container 402 from bulging and damage from forces external to flexible container 402, while the shape-memory alloy provides shape control of intercostal spacer device 400 in a center region 412. The fibers of the jacket comprise, for example, PET fabric, polypropylene fabric, polyethylene fabric and/or steel, titanium or other metal wire. Depending on the application, structure 404 may be permeable to a desired degree. For example, if bone or tissue growth is desired to attach to structure 404, permeability to the tissue or bone of interest would be appropriate. As another example, permeability of structure 404 may be desired to allow the material used to fill flexible container 402 to evacuate air or water, for example, from flexible container 402, in order to prevent bubbles from forming inside. Where a mesh is used, for example, the degree of permeability desired can be achieved by loosening or tightening the weave.

Although structure 404 is shown in a roughly H-shape in the example of FIG. 8, it will be understood that in practice, structure 404 can be made to be folded, unexpanded, or otherwise compacted. This is particularly true where, for example, structure 404 comprises a fabric or other easily folded material. A folded or unexpanded state facilitates implantation, allowing for a smaller surgical opening, and unfolding or expansion in situ upon filling of flexible container 402. Further, structure 404 can have a different final shape, depending on the shape-control material used. For example, the shape-memory wires in FIG. 8 may be in their inactive state, whereupon activation by body temperature causes contraction thereof, making the spacer of FIG. 8 "thinner" than shown in center region 412.

Figure 9:
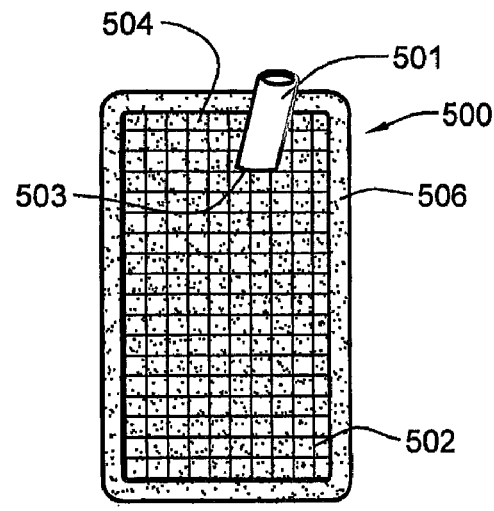
FIG. 9 is a posterior elevational view of one embodiment of an intercostal spacer device with an integrated container and structure, in accordance with an aspect of the present invention.

FIG. 9 depicts an outer view of another example of an intercostal spacer device 500 in accordance with an aspect of the present invention. A flexible container conduit 501 is shown pointing outward from an opening 503. As shown, the structure 502 delimits the final shape of intercostal spacer device 500. Structure 502 comprises a mesh 504 of shape-memory alloy wire, that is soaked through with a dispersion polymer 506 (e.g., silicone). The dispersion polymer (after curing) acts as the flexible container and is shown filled in FIG. 9. This is one example of the flexible container and structure 502 being integral. Although mesh 504 of FIG. 9 is described as being all shape-memory alloy wire, it will be understood that, like FIG. 8, the shape-memory alloy could only form a part of structure 502.

Figure 10:
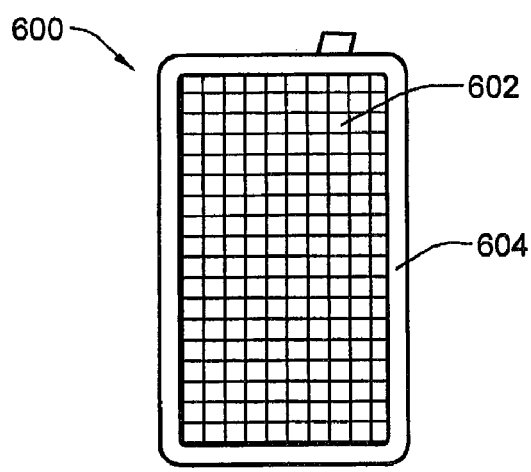
FIG. 10 is a cross-sectional elevational view of one embodiment of an intercostal spacer device with an external container, in accordance with an aspect of the present invention.

FIG. 10 is a cross-sectional view of another example of an intercostal spacer device 600 in accordance with the present invention. Intercostal spacer device 600 is similar to intercostal spacer device 500 of FIG. 9, except that instead of being soaked in a dispersion polymer, a structural mesh 602 of a shape-memory alloy wire is coated with a dispersion polymer (e.g., silicone) 604 or other curable liquid appropriate for the container material, creating an outer flexible container. The coating can be done in a conventional manner, for example, by dip molding on the outside of the mesh.

Figure 11:
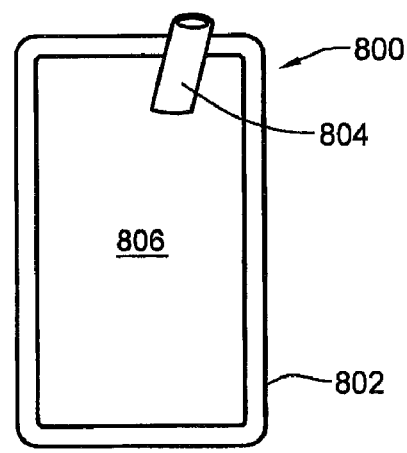
FIG. 11 depicts another embodiment of an intercostal spacer device with an integrated container and structure, in accordance with another aspect of the present invention.

FIG. 11 depicts yet another example of an intercostal spacer device 800 with an integrated flexible container and structure, in accordance with another aspect of the present invention. The flexible container and structure in the example of FIG. 11 both comprise a single layer 802 of rubber that is thick enough for a given application to perform the functions of both the flexible container and structure (including shape control). Such a rubber shell would be able to return to its original shape when unconstrained. In addition, intercostal spacer device 800 preferably includes a conduit 804 (preferably, a one-way valve) for filling the internal space 806. The injectable material can be any of the filling materials described above, for example, silicone.

In an alternate aspect, the rubber shell 802 of FIG. 11 can be augmented with internal, external, or integrated features to further control shape. Examples of such features include thread, wires (e.g., metal, including shape-memory alloys), cables, tethers, rings or a mesh.

The method for correcting a spinal deformity utilizing an alternative embodiment of the intercostal spacer device includes, providing at least one intercostal spacer device 400, the intercostal device 400 includes a flexible container 402 used to contain an injectable material, with flexible container 402 being preferably impermeable to the injectable material, a conduit 406 coupled to flexible container 402 for receiving the injectable material and a structure 404, that controls at least part of flexible container 402 after injectable material is injected through conduit 406 and into flexible container 402. Structure 404 has a shape that is sized and configured for placement between two adjacent ribs of a patient. The method preferably provides for intercostal spacer device 400 to be implanted into the intercostal space between two adjacent ribs. The method would also typically include injecting the injectable material preferably through conduit 406 into flexible container 402, the injectable material being compressible following intercostal spacer device 400 implantation between two adjacent ribs. The compressibility characteristic ensures that the injectable material exhibits viscoelastic behavior and that, along with structure 404, the intercostal spacer device 400 can accept compressive loads and produce distraction forces for correcting a spinal deformity within a patient.

The disclosures of application Ser. Nos. 11/438,940, filed May 23, 2006; 11/438,891, filed May 23, 2006; and 11/104,267, filed Apr. 12, 2005 are all incorporated herein in their entirety.

Although the preferred embodiments have been depicted and described in detail herein, it will be apparent to those skilled in the relevant art that various modifications, additions and substitutions can be made without departing from its essence and therefore these are to be considered to be within the scope of the following claims.

What is claimed is:

1. An intercostal spacer device for use in correcting a spinal deformity comprising:
a spacer member having an exterior, wherein the exterior includes a posterior face and an opposite anterior face facing away from the posterior face;
first and second pairs of arms extending upwardly from the spacer member and spaced from each other; the first and second pair of arms forming first and second channels respectively, the first and second channels being disposed between the posterior face and the anterior face;
a third pair of arms extending downwardly from the spacer member; the third pair of arms forming a third channel extending parallel to the first and second channels;
a fourth channel extending from the posterior face to the anterior face such that the fourth channel extends through the exterior surface and wherein the fourth channel extends transverse to the first, second, and third channels and separates the first channel from the second channel;
a theoretical plane extending through the spacer and bisecting a distance between the first and second channels, the third pair of arms extending through the theoretical plane;
the first and second channels each having a depth measured in a direction from the third pair of arms toward the first and second pair of arms, the depths of the first and second channels being substantially the same;
wherein the spacer member, first pair of arms, second pair of arms, and third pair of arms are sized and configured to allow for placement of the intercostal spacer device between two adjacent ribs of a patient to dynamically produce a force for correcting a spinal deformity of the patient.

2. The intercostal spacer device of claim 1 wherein:
the first pair of arms includes a first anterior arm and a first posterior arm, the first anterior arm and the first posterior arm being substantially parallel to each other and forming the first channel therebetween, and wherein the first channel is sized to receive a first rib of the two adjacent ribs,
the second pair of arms includes a second anterior arm and a second posterior arm, the second anterior arm and the second posterior arm being substantially parallel to each other and forming the second channel therebetween, and wherein the second channel is sized to receive the first rib of the two adjacent ribs,
and wherein the third pair of arms includes a third anterior arm and a third posterior arm, with the third anterior arm and the third posterior arm extending substantially parallel to each other and forming the third channel therebetween, wherein the third channel is sized to receive a second rib of the two adjacent ribs of the patient.

3. The intercostal spacer device of claim 2 wherein the first, second, and third posterior arms are configured for positioning along a posterior side of the first and second ribs; wherein the first, second, and third anterior arms are configured for positioning along an anterior side of the first and second ribs.

4. The intercostal spacer device of claim 1 wherein the intercostal spacer device is fabricated from a flexible material.

5. The intercostal device of claim 1 wherein the first, second, and third pairs of arms are integrally formed with the spacer member.

6. The intercostal spacer device of claim 1 wherein the first and second pairs of arms extend substantially parallel to the theoretical plane.

7. The intercostal spacer device of claim 6 wherein the third channel intersects the theoretical plane.

8. An intercostal spacer system, the intercostal spacer system comprising:
a plurality of intercostal spacer devices, the plurality of intercostal spacers including a first intercostal spacer device and a second intercostal spacer device, distinct from the first intercostal spacer device;

wherein the first intercostal spacer device comprises:
- a first spacer member having a first exterior, wherein the first exterior includes a first posterior face and an opposite first anterior face facing away from the first posterior face;
- first and second pairs of arms extending upwardly from the first spacer member and spaced from each other; the first and second pairs of arms forming first and second channels respectively;
- a third pair of arms extending downwardly from the first spacer member; the third pair of arms forming a third channel extending parallel to the first and second channels;
- a fourth channel extending from the first posterior face to the first anterior face such that the fourth channel extends through the first exterior surface and wherein the fourth channel extends transverse to the first, second, and third channels and separates the first channel from the second channel;
- the first and second channels having first and second depths respectively, the first and second depths being measured in a direction from the third channel toward the fourth channel, and the first and second depths being substantially the same;
- the fourth channel having a third depth along the first posterior face and a fourth depth along the first anterior face, the third and fourth depths measured in a direction from the third channel toward the fourth channel, the third and fourth depths being substantially the same;
- wherein the first spacer member, first pair of arms, second pair of arms, and third pair of arms are sized and configured to allow for placement of the first intercostal spacer device between first and second adjacent ribs of a patient;

wherein the second intercostal spacer device comprises:
- a second spacer member having a second exterior, wherein the second exterior includes a second posterior face and an opposite second anterior face facing away from the second posterior face;
- fourth and fifth pairs of arms extending upwardly from the second spacer member and spaced from each other; the fourth and fifth pairs of arms forming fifth and sixth channels respectively;
- a sixth pair of arms extending downwardly from the second spacer member, the sixth pair of arms forming a seventh channel extending parallel to the fifth and sixth channels;
- an eighth channel extending from the second posterior face to the second anterior face such that the eighth channel extends through the second exterior surface and wherein the eighth channel extends transverse to the fifth, sixth, and seventh channels and separates the fifth channel from the sixth channel;
- the fifth and sixth channels having fifth and sixth depths respectively, the fifth and sixth depths being measured in a direction from the seventh channel toward the eighth channel, and the fifth and sixth depths being substantially the same;
- the eighth channel having a seventh depth along the second posterior face and an eighth depth along the second anterior face, the seventh and eighth depths being measured in a direction from the seventh channel toward the eighth channel, and the seventh and eighth depths being substantially the same;
- wherein the second spacer member, the fourth pair of arms, the fifth pair of arms, and the sixth pair of arms are sized and configured to allow for placement of the second intercostal spacer device between the second rib and an adjacent third rib of the patient.

9. The intercostal spacer system of claim 8 wherein the second intercostal device is shaped substantially identical to the first intercostal device.

10. The intercostal spacer system of claim 8 wherein the first intercostal device further comprises a central axis extending vertically through a center of the spacer member such that the first pair of arms is disposed on a first lateral side of the central axis, the second pair of arms is disposed on a second lateral side of the central axis, and the third pair of arms is aligned with the central axis.

11. The intercostal spacer system of claim 8 wherein the first and second intercostal spacer devices are fabricated from a flexible material.

12. The intercostal spacer system of claim 8 wherein the first, second, and third pairs of arms are integrally formed with the first spacer member and the fourth, fifth, and sixth pairs of arms are integrally formed with the second spacer member.

13. An intercostal spacer device for use in correcting a spinal deformity comprising:
- a central body connecting opposed first and second flanges, the central body disposed between the first and second flanges; an exterior surface of the first flange forming a posterior face of the spacer device and an exterior surface of the second flange forming an anterior face of the spacer device, the posterior face facing away from the anterior face;
- a first upper channel formed by an upper surface of the central body and the first and second flanges, wherein the first upper channel has a first depth measured upwardly from the upper surface of the central body;
- a second upper channel formed by the upper surface of the central body and the first and second flanges, wherein the second upper channel has a second depth measured upwardly from the upper surface of the central body and the second depth is substantially the same as the first depth;
- an upper gap separating the first and second upper channels, the upper gap extending from the posterior face to the anterior face such that the upper gap extends through the exterior surfaces of the first and second flanges, the upper gap having a third depth measured upwardly along the posterior face and a fourth depth measured upwardly along the anterior face, the third and fourth depths being substantially the same;
- a lower channel formed by a lower surface of the central body and the first and second flanges; wherein the lower channel extends parallel to the first and second upper channels;
- wherein the first and second upper channels are configured for receiving a first rib of a pair of adjacent ribs when the intercostal spacer device is placed between the first pair of ribs with the central body extending between the first pair of ribs;
- wherein the lower channel is configured for receiving a second rib of a pair of adjacent ribs when the intercostal spacer device is placed between the first pair of ribs with the central body extending between the first pair of ribs.

14. The intercostal spacer device of claim 13 wherein, when viewed normal to the first flange, the lower channel is disposed laterally between the first and second upper channels.

15. The intercostal spacer device of claim 13 wherein, when viewed normal to the first flange, the lower channel intersects a theoretical vertical axis extending through a center of the central body and the first and second upper channels are laterally offset from the theoretical vertical axis.

16. The intercostal spacer device of claim 13 wherein the lower channel is sized to be received in an upper gap of an identically configured second intercostal spacer.

17. The intercostal spacer device of claim 13 wherein the first and second flanges are integrally formed with the central body.

18. The intercostal spacer device of claim 13 further comprising a theoretical plane extending through the spacer and bisecting a distance between the first and second upper channels.

19. The intercostal spacer device of claim 18 wherein the lower channel has a length extending transverse to the upper gap and extending substantially parallel to the first and second upper channels and wherein the theoretical plane bisects the length of the third channel.

* * * * *